Figure 1:
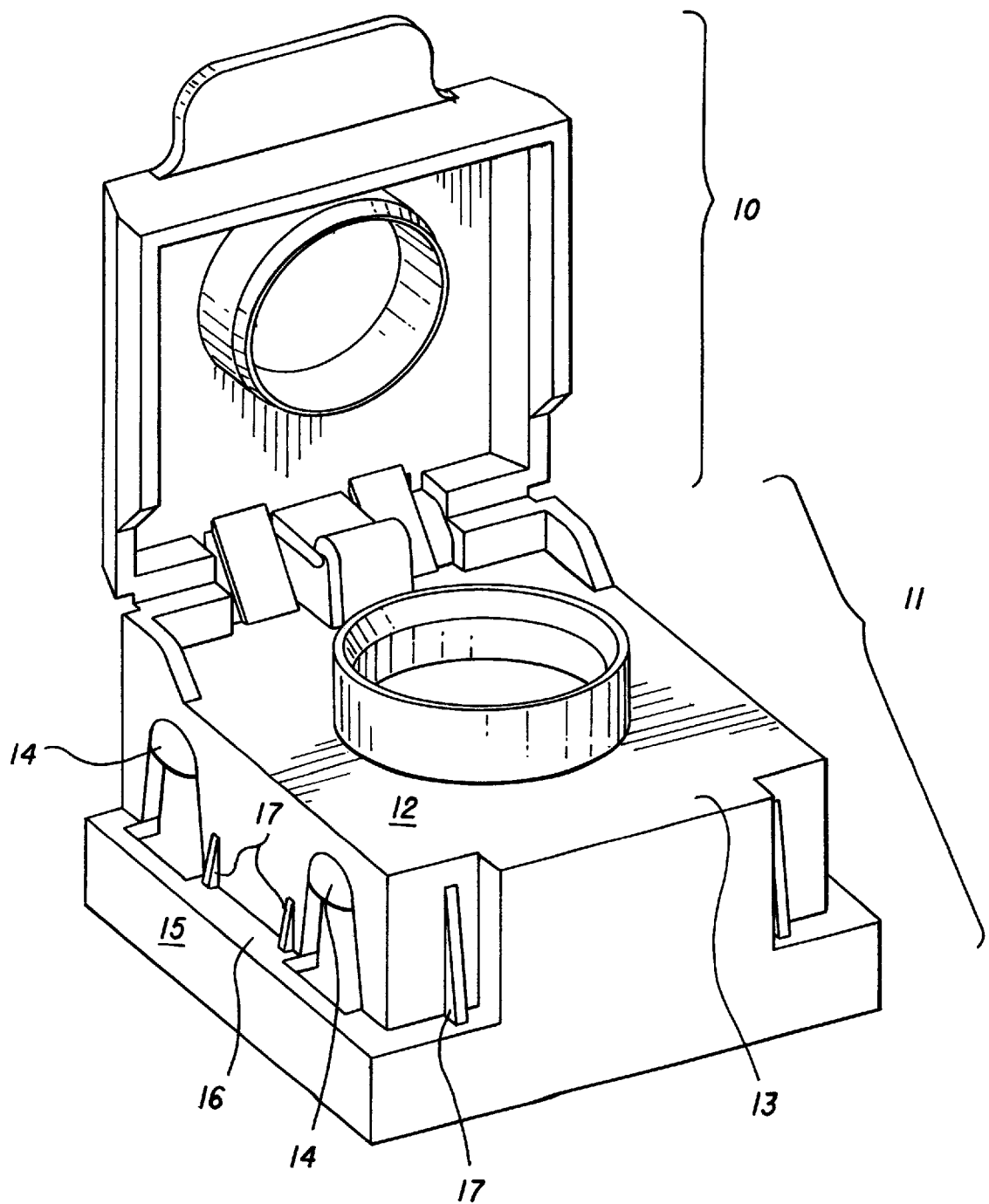

US005862934A

United States Patent [19]
Sattler et al.

[11] Patent Number: 5,862,934
[45] Date of Patent: *Jan. 26, 1999

[54] PACKAGING SYSTEM FOR LIQUID REAGENTS

[75] Inventors: Stephan Sattler, Peissenberg; Albert Wohland, Viernheim; Hermann Erb, Fussgönnheim, all of Germany

[73] Assignee: Boehringer Mannheim GmbH, Mannheim, Germany

[*] Notice: This patent issued on a continued prosecution application filed under 37 CFR 1.53(d), and is subject to the twenty year patent term provisions of 35 U.S.C. 154(a)(2).

[21] Appl. No.: 502,879

[22] Filed: Jul. 17, 1995

[30] Foreign Application Priority Data

Jul. 16, 1994 [DE] Germany ............ 44 25 277.3

[51] Int. Cl.[6] .................................... A47G 19/00
[52] U.S. Cl. .................... 220/23.4; 215/395; 206/216
[58] Field of Search ................. 215/395, 399; 220/23.2, 23.4; 206/216

[56] References Cited

U.S. PATENT DOCUMENTS

| 2,166,616 | 7/1939 | Wallace | 220/23.2 X |
| 2,462,956 | 3/1949 | Gross | 220/23.4 |
| 2,577,120 | 12/1951 | Franz | 220/23.2 X |
| 2,874,835 | 2/1959 | Poupitch | 220/23.4 X |
| 2,949,204 | 8/1960 | Edwards | 220/23.4 X |
| 3,630,350 | 12/1971 | Bolton | 220/23.2 X |
| 3,751,098 | 8/1973 | Owen | 220/23.4 X |
| 4,784,260 | 11/1988 | Holben | 220/23.4 X |
| 4,785,953 | 11/1988 | Buchhdz et al. | 220/23.4 X |
| 4,941,585 | 7/1990 | Hare et al. | 220/23.2 |
| 4,986,432 | 1/1991 | Anghileri | 220/23.4 |
| 5,294,404 | 3/1994 | Grandone et al. | |
| 5,322,668 | 6/1994 | Tomasso . | |

FOREIGN PATENT DOCUMENTS

| 0 290 019A2 | 11/1988 | European Pat. Off. . |
| 0 517 092A1 | 12/1992 | European Pat. Off. . |
| 44 11 188A1 | 10/1994 | Germany . |
| 49-52961 | of 1974 | Japan . |
| 50-71327 | of 1975 | Japan . |
| WO93/01739 | 2/1993 | WIPO . |

*Primary Examiner*—Stephen K. Cronin
*Attorney, Agent, or Firm*—Nikaido, Marmelstein, Murray & Oram LLP

[57] ABSTRACT

Packaging system for liquid reagents in which two or more vessels with holding areas are combined by pressing a plug-on plate onto the holding areas of the vessels. For this purpose the plug-on plate has two or more apertures the cross-section of which essentially corresponds to the cross-section of the holding areas of the vessels. Plug-on plate and/or holding areas of the vessels can have stop elements which, after the combination, hinder the separation vessels and plug-on plate.

27 Claims, 4 Drawing Sheets

PACKAGING SYSTEM FOR LIQUID REAGENTS

The present invention concerns a packaging system for liquid reagents comprising one or several vessels with a holding area and a plug-on plate with a number of apertures that correspond to the number of vessels, wherein the apertures in the plug-on plate essentially correspond in size and shape to the cross-section of the holding areas.

Packaging systems for liquid reagents are mainly required in clinical analytics since in this case a multitude of liquid vessels have to be handled manually and mechanically. In the state of the art packaging systems for liquid reagents are known from U.S. Pat. No. 4,849,177 and WO 93/01739. A container is described in the U.S. Pat. No. 4,849,177 which has several depressions in which the reagent containers can be placed. The container envelopes the bottom and peripheral surfaces of the vessels. Due to the shape of the depressions, the container is designed for vessels with a circular cross-section.

The international application WO 93/01739 also describes a container into which vessels are placed. In order to utilize the described packaging system, the vessels are placed in the container and a cover plate is placed thereon. Cylinders are located on the underside of the cover plate which are placed over the necks of the reagent vessels and thus lead to a positioning of the reagent vessels in the container.

Therefore the state of the art has the disadvantage that in order to combine vessels a container is needed into which the vessels are placed. This is associated with the use of a relatively large amount of material for the necessary container. The described arrangements in addition need a relatively large amount of space. Furthermore the state of the art has the disadvantage that markings on the vessels which indicate the bottle contents are covered by the containers. Therefore an additional marking on the outside of the container is necessary.

The object of the invention was to overcome the disadvantages of the state of the art. It was in particular the object of the invention to enable reagent vessels to be joined together in a manner which needs less material and is cost-effective. Moreover it was the object of the invention to enable simple combinations for the user and to propose a system that allows a rapid and simple interchange or new combination of liquid reagents.

The present invention proposes a packaging system for liquid reagents which comprises one or several vessels with a holding area and a plug-on plate with a number of apertures that corresponds to the number of vessels, the apertures in the plug-on plate corresponding essentially in size and shape to the cross-section of the holding areas.

In addition the invention proposes a process for joining together reagent vessels in which a plug-on plate with two or more apertures is pressed onto the holding areas of reagent vessels.

The invention concerns the packaging of liquid reagents. Particularly in clinical analytics it is necessary to reliably handle a multitude of different reagent vessels in connection with automated analysers. This means that the vessels have to be reliably transported and positioned in the automated analyser. In addition it must be ensured that the vessels can be identified by an identification mark. Said requirements can be ensured and facilitated by joining together individual vessels to form combinations of two or several vessels. This is achieved in the present invention by placing a plug-on plate onto the vessels which holds the vessels in a defined configuration relative to one another.

The area of clinical chemistry sets a number of requirements for the instruments and reagents used resulting in requirements for the instruments used which differ greatly from the requirements for example in the field of foodstuffs. The said liquid reagents have a highly complex composition that is subject to production-related variations. In addition liquid reagents in general have a limited shelf life. The said reasons result in the necessity to provide liquid reagents with an identification number, to mark the vessel with production-related details and also, if necessary, to label the vessels with the expiry date. This labelling is usually achieved by a one-dimensional or two-dimensional barcode, magnetic strips or so-called RF-ID chips.

Liquid reagents within the sense of the present invention are all liquids that take part directly or indirectly in the analysis. These are in particular liquids which react with samples in a pre-defined manner but they, however, also include those liquids which serve to calibrate the automated analyser. It is also intended to include wash liquids and other auxiliary liquids.

Vessels within the sense of the invention are understood as open or closed containers that serve as a receptacle for liquids. The vessels preferably have a cylindrical shape with a round, square, trapezoid or rectangular cross-section. The vessels have a storage area in which the liquid is located, a holding area which, acting together with the plug-on plate, serves to hold the vessels. The vessels also usually have a closure area. Devices known from the state of the art can be used as the closure. These are for example hinged covers, screw caps and stoppers. In particular the hinged covers described in the German Patent Application file number P 44 19 116.2 are advantageous for use in packaging systems according to the invention. Reference is herewith made in full detail to the said German Patent Application.

The storage area of the vessels in general has a cylindrical shape with a round, square, trapezoid or rectangular cross-section. Holding areas are also advantageous for special applications in which the outer shape and inner shape of the vessels differ. In some applications it is advantageous according to the invention when the outer wall of the storage container is a cylinder with a square base area whereas the inner storage space is a cylinder with a round base area. In this way it can be ensured, even for small filling volumes, that the vessel has an adequate size in order to ensure easy handling. In general flat surfaces are preferred on the outside of the storage area since labels such as bar-codes can be applied more easily and can also be read easier.

It is preferred according to the invention when vessels having the same outer shape are used for the packaging system. Such a standardization makes it possible to simplify production processes as well as to also extremely simplify the automatic handling of the vessels within an automated analyser. Round or square cross-sections of the vessels are preferred for handling the vessels during filling and transport since in these cases the vessels do not have to be aligned. It is also advantageous when the apertures in the plug-on plate have the same or at least nearly the same cross-section so that the holding area of each of the vessels can be inserted into each aperture in the plug-on plate.

The vessels for liquid reagents are combined according to the invention by a plug-on plate. The plug-on plate has one or several, preferably two or three, apertures that essentially correspond in size and shape to the cross-section of the holding areas of the vessels. Apertures are preferred which essentially have a rectangular cross-section. The size of the apertures is usually in the range of a few centimetres. The apertures preferably have smaller area parts which reduce the symmetry of the aperture. An aperture can for example have a rectangular cross-section which has a side bar as an additional area element. When the holding area of a vessel has the same cross-section, then the plug-on plate can only be pressed onto the holding area in one orientation. This ensures an unequivocal orientation of the vessels relative to one another and to the plug-on plate. The apertures can for example have a trapezoid or oval cross-section in order to ensure a desired orientation of vessels and plug-on plate.

A packaging system has also proven to be advantageous in which the plug-on plate has apertures whose cross-section has a $C_2$ axis perpendicular to the plane of the cross-section. This can for example be realized by a rectangular aperture or a square aperture with two side bars that face each other. If the holding areas of the vessels correspondingly have a rectangular cross-section or a square cross-section with one or two apertures for the side bars, then the vessels can be linked with the plug-on plate in two positions. These positions result from rotating the vessel along its longitudinal axis. These informations enable a person skilled in the art to give a multitude of possibilities for the cross-section of the apertures on the plug-on plate and for the cross-section of the holding areas that fulfil the same function.

The plug-on plate can advantageously be constructed in such a way that the peripheral areas of the apertures and, if desired, also the outer edge of the plug-on plate, are thickened. This increases the mechanical stability of the plug-on plate and requires less material. Moreover, thickening the material at the edge of the apertures increases the surfaces of the holding areas of vessels and plug-on plate that lie adjacent to one another. This increases the stability of a packaging system according to the invention.

The plug-on plate can also have guiding elements which enable a packaging system according to the invention to be positioned and/or transported within an automated analyser. These guiding elements can for example be additional apertures in the plug-on plate. It is also possible to provide projections, bars or such like on the plug-on plate.

Plastics such as polyethylene, polypropylene, polystyrene and polymethylmethacrylate are suitable as materials for the vessel and the plug-on plate. However, it is also possible to manufacture the plug-on plate from metals. If desired, mixtures of these plastics and auxiliary substances known to a person skilled in the art can also be used which contribute to an increase in the strength, rigidity or flatness. Glass can in particular be used for the storage area of the vessels in addition to plastic. Due to the higher mechanical stress, high quality plastics in particular are suitable for the closure and holding area. The plastics polyethylene and polypropylene are particularly suitable for closures with film hinges.

Vessels for use in a packaging system according to the invention can be constructed as single, double or multiple parts. Those vessels are particularly preferred in which a unit comprising closure and holding area is inserted onto a storage area.

The holding area has constructive elements which are adapted to the plug-on plate so that it is possible to lock the plug-on plate and holding area.

A central aspect of the invention is the interaction between holding area and plug-on plate in order to hold the vessels. In order to achieve this manner of function two embodiments are particularly suitable:

In the first embodiment the holding area has constructional elements which are at an angle to the longitudinal axis of the vessel. These construction elements can for example be surfaces or bars. Due to these constructional elements the cross-section of the holding area varies. In a first zone the cross-section of the holding area is smaller than the inside cross-section of the aperture in the plug-on plate. In another zone the holding area has a cross-section that corresponds to the inside width of the aperture or extends beyond it. When the plug-on plate is pressed onto the side of the holding area which has a smaller cross-section and it is moved in the direction of the larger cross-section, then this locks the plug-on plate and holding area. If bars are used as constructional elements, then the cross-section of the holding area and the cross-section of the aperture are essentially identical. The bars run in such a way that one side is aligned with the peripheral surface of the holding area and they rise across the width of the holding area so that at the opposite end they protrude above the peripheral surface of the holding area by a few millimetres. When plug-on plate and vessel are linked together according to the invention, then the bars and plug-on plate are interlocked. A connection that is free from play can be achieved in this way even when the partners that make the connection, i.e. plug-on plate and holding area, display manufacturing tolerances.

In a second embodiment one or several ramps are arranged on the side of the holding area facing the closure. One side of the ramps aligns with the peripheral surface and the opposite side rises a few millimetres above the peripheral area. When the plug-on plate is moved over the closure of a vessel and towards the holding area, then it is possible to move the plug-on plate over the ramps with a relatively small force. When the ramps have been overcome the plug-on plate reaches a stop position from which it can only be moved by exerting a larger force due to the steeply rising sides of the ramps. The side of the holding area opposite the ramps is advantageously bounded by a material projection. Therefore in the stop position the plug-on plate is between the material projection and ramps.

A particularly preferred embodiment of the holding area results by combining the said embodiments with each other.

A packaging system according to the invention has the advantage according to the aforementioned that it enables vessels to be combined in an easy and material-saving manner. In addition a packaging system according to the invention is space-saving and thus enables a reduction in size of automated analysers in which it is used.

The packaging system according to the invention also has the advantage that it ensures a defined orientation of the reagent vessels relative to one another and relative to the plug-on plate. Moreover it is especially important that the system according to the invention enables an exact positioning of the mouths of the bottles and the closures. Furthermore it is advantageous that large areas of the vessels are accessible from the outside so that labels on the vessels can be read.

A further favourable feature of the system is that a linkage between vessels and plug-on plate can be detached again. This for example enables vessels to be joined together in new combinations or individual vessels in a configuration to be exchanged. It is possible to exchange vessels very simply and also rapidly using the packaging system according to the invention. In practice it is often desired that it should not be possible to easily alter a configuration joined together by the manufacturer or customer. In this case the stop elements which hold the plug-on plate on the holding area can be designed in such a way that a vessel can only be removed from the configuration when a considerable force is exerted.

The invention is elucidated in more detail by the following figures.

Figure 2:
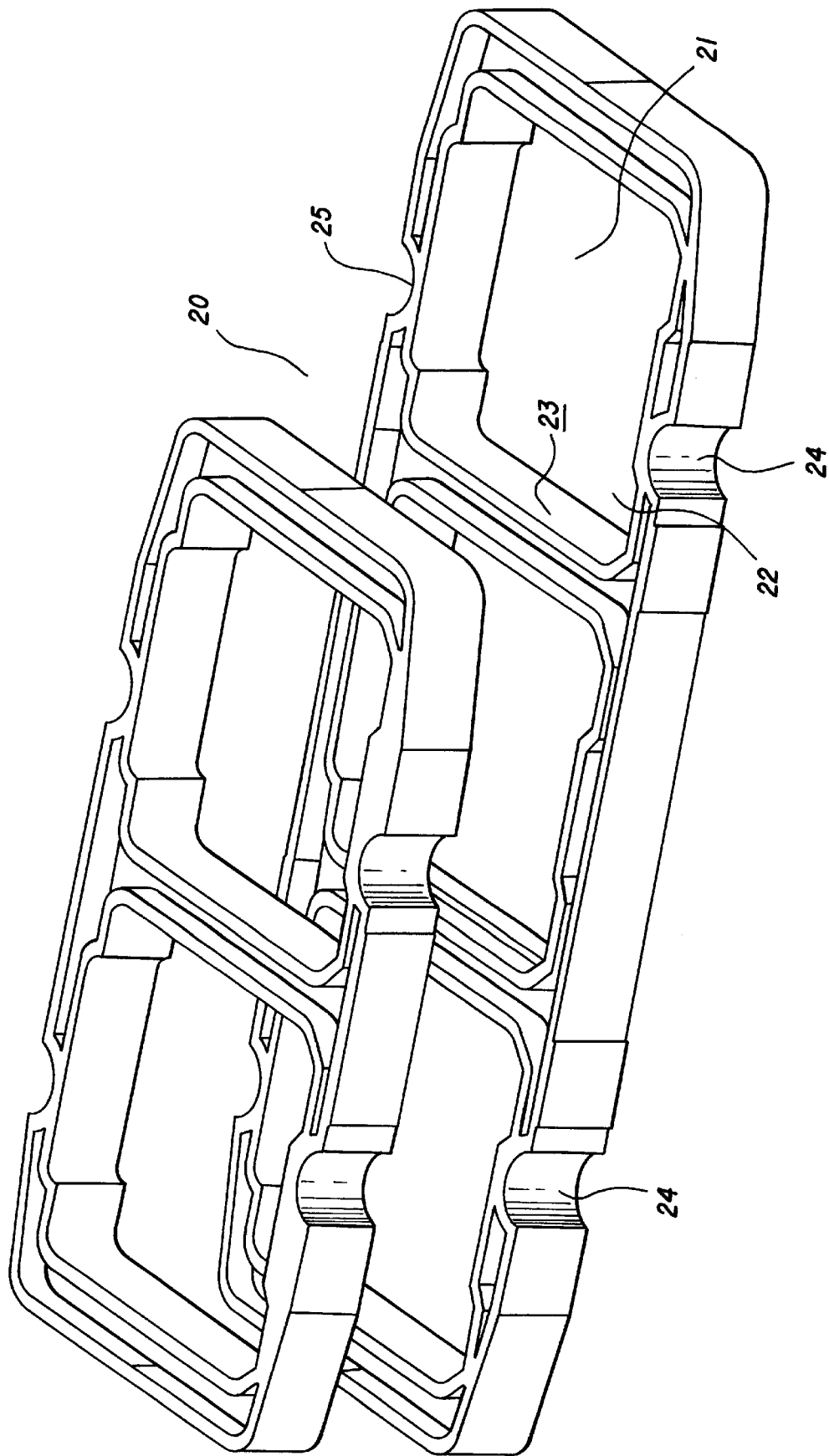
Figure 3:
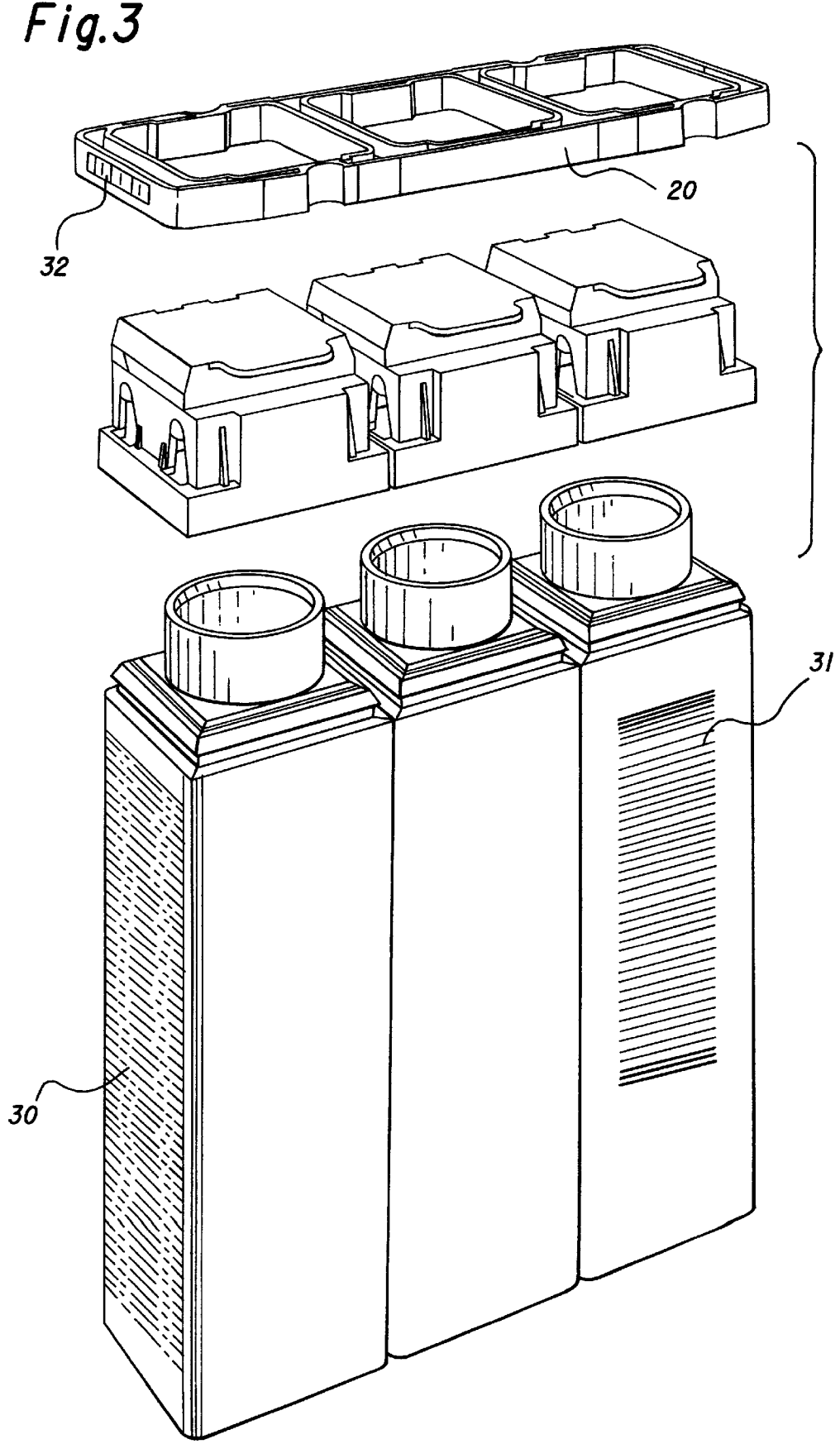

FIG. 1 unit of closure area and holding area
FIG. 2 plug-on plates
FIG. 3 exploded view of a packaging system
FIG. 4 top-view of embodiments for plug-on plates
FIG. 5 system of plug-on plate and vessel with which there are two possible positions for each vessel within an aperture.

FIG. 1 shows a unit comprising a closure area (10) and a holding area (11). This unit can be pressed onto the storage area of a vessel and then results in a closable vessel with a holding area. The holding area (11) shown in FIG. 1 has a base (12) in the upper part which has a rectangular shape in cross-section which is adjoined by a projection (13). Two ramps (14) are located on each of the opposite side walls of the base which protrude above the side surface of the base (12). In the lower part of the holding area (11) there is a second base (15) which also has a rectangular cross-section that is larger than that of the base (12). This results in a projection of material (16).

Furthermore side bars (17) can be seen in FIG. 1 the outer sides of which are inclined relative to the longitudinal axis of the vessel. The outer wall of the bars (17) at the upper side of the holding area is on a plane with the base (12). Towards the underside of the holding area the bars protrude from the base (12).

FIG. 2 shows a plug-on plate with two apertures and a plug-on plate with three apertures. It can be seen from both plug-on plates that the outer edges and the edges facing the apertures are thickened in relation to the base area of the plug-on plate. From aperture (21) it can be seen that its shape corresponds to that of the upper base (12) of the holding area. This means that aperture (21) has a rectangular cross-section adjoined by an element of area (22) into which the projection (13) fits when the plug-on plate (20) is pushed onto the holding area (11). The rim surface (23) of the aperture (21) has a width that corresponds to the distance between the projection of material (16) and the lower edge of the ramp (14). In addition the plug-on plate (20) has guiding elements (24, 25) on its front and back. In the present case the guiding elements are semi-circular apertures. If a packaging system according to the invention is used in an automated analyser, then for example rods of the automated analyser can engage in the guiding elements (24, 25) and serve to position the packaging system. The guiding elements (24) on the front have a different distance between each other than the guiding elements (25) at the back. In this way it is possible to distinguish between the front and back of the packaging system which enables an unequivocal orientation of the packaging system in an automated analyser.

The connection of plug-on plate (20) and holding area (11) is elucidated in more detail with the aid of FIGS. 1 and 2.

In order to fit the plug-on plate (20) and vessel together, the aperture (21) is inserted from the top onto the holding area (11). When the rim surface (23) is on the other side of the ramps (14) then further movement is prevented by the projection (16). The ramp (14) in turn prevents the plug-on plate (20) from slipping from the holding area. However, when an adequate amount of force is used, the holding area (11) and plug-on plate (20) can be separated from each other by pulling off the plug-on plate. When the plug-on plate (20) is pressed onto the holding area (11), the side bars (17) lock together the plug-on plate and holding area which leads to an additional stabilization of the connection.

FIG. 3 shows an exploded view of a packaging system according to the invention. In order to link the system together, firstly the unit comprising closure area and holding area is pressed onto the storage vessels (30). In a subsequent step the plug-on plate (20) is pressed onto the holding areas. As can be seen from the diagram, the vessels are arranged next to each other. The interaction between plug-on plate and holding areas results in the vessels having the same orientation.

Bar-code labels (31) on the storage vessels (30) are also shown in FIG. 3. It can be ensured by the packaging system according to the invention that the bar-code labels (31) are arranged on one side of the system and that they are positioned suitably for reading by a bar-code reader within an automated analyser. A bar-code label (32) can be applied to the plug-on plate that carries information that is characteristic for the packaging system whereas the bar-codes (31) carry vessel-specific informations. The label (32) can for example also contain information as to which different vessels are to be combined by the plug-on plate to form a packaging system. This for example allows a mechanical joining-together of individual vessels to form a packaging system according to the invention.

Figure 4A:
Figure 4B:
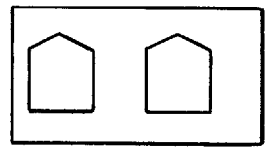
Figure 4C:
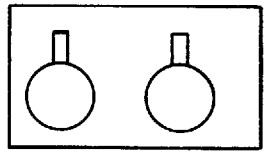

FIG. 4 shows three different designs for plug-on plates in a top view. The apertures of the plug-on plate in FIG. 4a have a trapezoid cross-section. In FIGS. 4b and 4c plug-on plates are shown with a pentagonal cross-section and with a round cross-section with an attached tongue. The illustrated plug-on plates exemplify how it is possible to achieve an unequivocal orientation of the vessels relative to each other and within the plug-on plate by selection of the cross-section of the apertures and thus also of the cross-section of the holding areas.

Figure 5A:
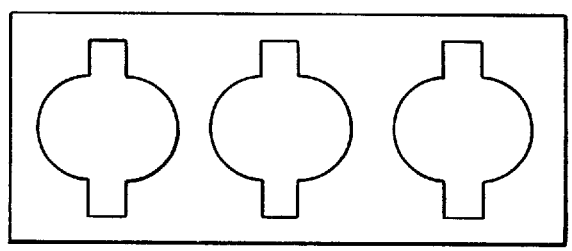
Figure 5B:
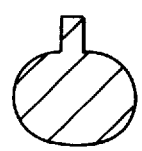
Figure 5C:
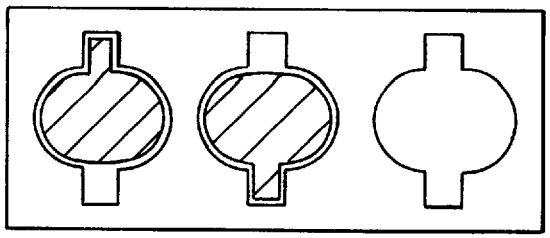

A plug-on plate is shown in FIG. 5a whose apertures are round and have two additional tongues. The vessel shown in top view in FIG. 5b can be connected with the plug-on plate in two different positions which are shown in FIG. 5c. Both the positions of the vessel shown in FIG. 5c are derived by turning the vessel on its longitudinal axis by 180°. This design can in particular be advantageous when two information carriers are applied to the vessel which can, however, only be read from one side in an analytical instrument. Thus it is possible to control which information carrier is read by inserting the vessels in the plug-on plate in a particular orientation.

LIST OF REFERENCES

(10) closure area
(11) holding area
(12) base
(13) projection
(14) ramps
(15) second base
(16) projection of material
(17) side bars
(20) plug-on plate
(21) aperture
(22) element of area
(23) rim surface of the aperture
(24, 25) guiding elements
(30) storage vessel
(31) bar-code label on storage vessel
(32) bar-code label on plug-on plate we claim:
1. A packaging system for liquid reagents, said system comprising:
   at least one reagent vessel, said reagent vessel including a closure section, a holding area, and a storage vessel; and a plug-on plate, said plug-on plate having at least one aperture therein, said at least one aperture corresponding in size and shape to a cross section of the holding area of the at least one reagent vessel, wherein the cross section of the holding area and the size and shape of the at least one aperture are configured to correspond to ensure an unequivocal orientation of the at least one vessel relative to said plug-on plate when said plug-on plate engages said holding area, wherein the at least one aperture and the cross section of the holding area are configured with corresponding engaging surfaces so as to prohibit relative rotation therebetween, and wherein said plug-on plate is configured such that said plug-on plate engages the holding area, and wherein, after engagement, a first end of the reagent vessel protrudes from a first side of the plug-on plate, and a second end of the reagent vessel protrudes upward from a second, opposite side of said plug-on plate.

2. A packaging system as recited in claim 1, wherein said holding area further comprises locking means projecting from a surface of the holding area, said locking means engaging a surface of said plug-on plate when said plug-on plate has been configured on said holding area.

3. A packaging system as recited in claim 1, wherein said at least one aperture of said plug-on plate includes a substantially rectangular cross section.

4. A packaging system as recited in claim 1, wherein said at least one aperture has a round cross section.

5. A packaging system as recited in claim 1, wherein said at least one vessel and said at least one aperture have corresponding cross sections, said cross sections being uniquely configured to eliminate rotation of the at least one vessel in the at least one aperture.

6. A packaging system as recited in claim 1, wherein the at least one plug-on plate and the at least one vessel have uniquely corresponding cross-sections such that the at least one vessel can engage the at least one aperture in a single predetermined axial orientation.

7. A packaging system as recited in claim 1, wherein said plug-on plate engages said holding area.

8. A packaging system as recited in claim 1, wherein said closure section and the holding area are a one-piece unit.

9. A packaging system as recited in claim 1, said system comprising a plurality of said vessels, and said plug-on plate comprising a plurality of apertures, with a number of said plurality of apertures corresponding to a number of said plurality of reagent vessels.

10. A packaging system as recited in claim 9, wherein each of said plurality of apertures has a cross-section which is identical to other of said plurality of apertures.

11. A packaging system as recited in claim 1, wherein said holding area includes securing means for securing the holding area to the plug-on plate.

12. A packaging system as recited in claim 11, wherein said securing means comprises inclined elements which are inclined relative to a longitudinal axis of the vessel, and which engage an inner peripheral surface of the at least one aperture of the plug-on plate.

13. A packaging system as recited in claim 1, wherein said holding area comprises limiting means which limits movement of the plug-on plate.

14. A packaging system as recited in claim 13, wherein said limiting means comprises a projecting element which projects outward from a surface of the vessel.

15. A packaging system for liquid reagents, said packaging system comprising:

at least one reagent vessel closure including a vessel holding area thereupon;

at least one reagent vessel, said reagent vessel having an open end which is configured to engage said at least one reagent vessel closure; and a plug-on plate, said plug-on plate having at least one aperture therein, said at least one aperture corresponding in size and shape to a cross section of the vessel holding area of the at least one reagent vessel closure, wherein the cross section of the vessel holding area and the size and shape of the at least one aperture are configured to ensure an unequivocal orientation of the at least one reagent vessel relative to the plug-on plate when the plug-on plate engages the holding area, wherein the at least one aperture and the cross section of the holding area are configured with corresponding engaging surfaces so as to prohibit relative rotation therebetween, and wherein said plug-on plate is configured such that said plug-on plate engages the holding area, and wherein, after engagement, a first end of the reagent vessel protrudes from a first side of the plug-on plate, and a second end of the reagent vessel protrudes upward from a second, opposite side of said plug-on plate.

16. A packaging system as recited in claim 15, wherein said plug-on plate engages said holding area.

17. A packaging system as recited in claim 15, wherein said closure and the holding area are a one-piece unit.

18. A packaging system as recited in claim 15, wherein said plug-on plate is configured such that said plug-on plate engages the holding area, and wherein, after engagement, a first end of the reagent vessel protrudes from a first side of the plug-on plate, and a second end of the reagent vessel protrudes upward from a second, opposite side of said plug-on plate.

19. A packaging system for liquid reagents, said system comprising:

at least one reagent vessel means, said reagent vessel means for supporting a reagent therein, said reagent vessel means including an outer peripheral portion; and plate support means for supporting said at least one reagent vessel means, said plate support means having at least one aperture therein, said at least one aperture corresponding in size and shape to the outer peripheral portion of the at least one reagent vessel means, wherein the outer peripheral portion of the at least one reagent vessel means and the size and shape of the at least one aperture in the plate support means are configured to ensure an unequivocal orientation of the at least one reagent vessel means relative to the plate support means when the plate support means engages the outer peripheral portion of the at least one reagent vessel means, wherein the at least one aperture and the cross section of the holding area are configured with engaging surfaces so as to prohibit relative rotation therebetween, and wherein said plug-on plate is configured such that said plug-on plate engages the holding area, and wherein, after engagement, a first end of the reagent vessel protrudes from a first side of the plug-on plate, and a second end of the reagent vessel protrudes upward from a second, opposite side of said plug-on plate.

20. A packaging system as recited in claim 19, wherein said plate support means engages a holding area of said reagent vessel means.

21. A packaging system as recited in claim 19, wherein said plate support means is configured such that said plate support means engages a holding area of the reagent vessel means, and wherein, after engagement, a first end of the reagent vessel means protrudes from a first side of the plate support means, and a second end of the reagent vessel means protrudes upward from a second, opposite side of said plate support means.

22. A plug-on-plate for supporting at least one vessel, said plug-on-plate comprising:

a plate having at least one aperture therein, said at least one aperture being configured to support a vessel, said aperture having a rectangular cross-section which corresponds to a cross section of said at least one vessel, and wherein said vessel is configured to contain liquid reagents, wherein the rectangular cross section of the aperture and the cross section of the at least one vessel are configured to correspond to ensure an unequivocal orientation of the vessel relative to the plate when the vessel engages the aperture, wherein the cross section of the aperture and the cross section of the at least one vessel are configured with corresponding engaging surfaces so as to prohibit relative rotation therebetween, and wherein the plate is configured such that the plate engages the holding area and wherein, after engagement, a first end of the at least one vessel protrudes from a first side of the plate, and a second end of the at least one vessel protrudes upward from a second, opposite side of the plate.

23. A plug-on-plate as recited in claim 22, comprising a plurality of said apertures for supporting a plurality of vessels, with each of said plurality of apertures having a rectangular cross-section which essentially corresponds to cross-sections of the plurality of vessels.

24. A plug-on-plate as recited in claim 22, wherein said plug-on-plate includes guiding means thereupon, said guiding means for guiding an external apparatus to a predetermined proximity of said vessel.

25. A plug-on-plate as recited in claim 22, said plug-on-plate including an identification means for identifying the plug-on-plate thereupon.

26. A plug-on-plate as recited in claim 25, wherein said identification means comprises a bar-code label.

27. A method for supporting a plurality of reagent vessels, said method comprising the steps of:

providing a plug-on-plate comprising a body with a plurality of apertures thereupon;

providing a plurality of reagent vessels, with a number of the reagent vessels corresponding to a number of the apertures provided in said plug-on-plate, each of said plurality of reagent vessels having a cross-section which corresponds to a cross section of each of the plurality of apertures in the plug-on-plate;

attaching said plug-on-plate to said plurality of reagent vessels, said attaching being performed by pressingly engaging an outer periphery of a portion of the reagent vessels with an inner periphery of the apertures, whereby said plug-on-plate supports said plurality of reagent vessels, wherein the cross section of said each of said plurality of reagent vessels and the corresponding cross section of said each of the plurality of apertures are configured to ensure an unequivocal orientation of said each of said plurality of reagent vessels into said corresponding one of the plurality of apertures in the plug-on-plate when said each vessel engages said corresponding aperture, wherein the cross section of said each of the plurality of apertures and the cross section of each of said each of said plurality of reagent vessels have corresponding engaging surfaces so as to prohibit relative rotation therebetween, and wherein the plug-on plate is configured such that the plug-on plate engages the plurality of reagent vessels with corresponding apertures, and wherein, after engagement, a first end of each of the plurality of reagent vessels protrudes from a first side of the plug-on plate, and a second end of each of the reagent vessels protrudes upward from a second, opposite side of said plug-on plate.

* * * * *